United States Patent
Hensel et al.

[11] Patent Number: 5,521,395
[45] Date of Patent: May 28, 1996

[54] METHOD AND APPARATUS FOR DETERMINING THE STRUCTURE OF YARNS IN THE REGION OF THEIR SURFACE

[75] Inventors: Rolf Hensel, Jona; Hans Wampfler; Peter Seitz, both of Zürich, all of Switzerland

[73] Assignee: Zellweger Luwa AG, Uster, Switzerland

[21] Appl. No.: 222,015

[22] Filed: Apr. 4, 1994

[30] Foreign Application Priority Data

Apr. 2, 1993 [CH] Switzerland .................. 01022/93

[51] Int. Cl.$^6$ ............................................... G01N 21/88
[52] U.S. Cl. .................. 250/562; 250/572; 250/208.2; 356/430
[58] Field of Search .................. 250/562, 563, 250/571, 572, 208.2; 356/385, 429, 430, 237; 28/187; 73/159

[56] References Cited

U.S. PATENT DOCUMENTS

| | | | |
|---|---|---|---|
| 3,985,451 | 12/1976 | Plöcki | 356/199 |
| 4,887,155 | 12/1989 | Massen | 358/107 |
| 5,030,841 | 7/1991 | Wampfler | 250/571 |

FOREIGN PATENT DOCUMENTS

| | | |
|---|---|---|
| 2443692 | 3/1976 | Germany . |
| 675133 | 8/1990 | Switzerland . |
| WO84/00781 | 3/1984 | WIPO . |
| WO91/12490 | 8/1991 | WIPO . |

*Primary Examiner*—Edward P. Westin
*Assistant Examiner*—Jacqueline M. Steady
*Attorney, Agent, or Firm*—Burns, Doane, Swecker & Mathis

[57] ABSTRACT

The surface of a yarn (G) is imaged on a sensor (7) having a plurality of sensor elements of differing structural arrangement. The signals of the individual sensor elements are compared with one another, and the structure of the examined yarn surface is determined on the basis of correspondence with the appropriate sensor element. The structure to be examined is formed both by the actual yarn surface and by the yarn edge, including projecting fibers and possible impurities, such as foreign fibers, included in the yarn.

9 Claims, 1 Drawing Sheet

METHOD AND APPARATUS FOR DETERMINING THE STRUCTURE OF YARNS IN THE REGION OF THEIR SURFACE

FIELD OF THE INVENTION

It is known that, where rotor yarns are concerned, it repeatedly happens that yarns having virtually identical measured values in the test of uniformity and nappiness produce sheet-like textile structures with a widely varying appearance and with properties different from one another (for example, in the so-called "feel"). It can be concluded from this that rotor yarns in particular largely lack a measure or parameter for characterizing the yarn surfaces appropriately in textile terms. At the present time, an aid adopted for determining the structure is a comparison between the theoretically set and the mechanically measured twist, this measurement being carried out by means of an untwisting and twisting method.

BACKGROUND

This untwisting and twisting method is not only inaccurate and time-consuming for rotor yarns but also leads to a destruction of the yarn to be examined and, therefore, no longer meets present-day requirements. Apart from that, particularly where rotor yarns are concerned, the twist, even if it were measured exactly, quickly and non-destructively, is not an ideal measure of the surface structure, because this is influenced to a substantially greater extent by other phenomena, such as, for example, the so-called wrapper fibers or wrapped fibers.

As regards ring yarns, the twist is likewise measured mechanically by untwisting and twisting, and mechanical methods are likewise known for twines (see EP-A-118,466). Moreover, optical methods for the on-line determination of twist fluctuations on machines are also known. Methods of this type are described in, for example, CH-A-675,133, WO-A-91/12490, U.S. Pat. No. 4,887,155 and DE-A-2,443, 692.

OBJECT AND SUMMARY OF THE INVENTION

The present invention relates to a method and apparatus for determining the structure of yarns in the region of their surface. A preferred embodiment relates, in particular, to the structure both of the actual yarn surface and of the yarn edge, including impurities or inclusions contained in the yarn or fibers projecting from the yarn. This preferred method works accurately, non-destructively and quickly and is thus also capable of being used for on-line measurement on running machines. Also, it allows the determination of parameters which can be used for characterizing the yarn surfaces appropriately in textile terms.

According to the invention, the surface is imaged on a sensor having a plurality of sensor elements of differing structural arrangements. The signals of the individual sensor elements are tested for correspondence with the examined structure, and the examined structure is determined by processing the signals supplied by the sensor elements.

The individual elements of the differing structural arrangements are, for example, differently oriented or masked. Thus, the sensor elements can be designed as stripe patterns with different angles of inclination or as differently inclined slit-shaped photodiodes for the measurement of twist. For determining other structural features, such as, for example, wrapper fibers, the sensor element may simulate different typical wrapper fibers.

The procedure for determining the yarn structure can use only sensors for a specific parameter; the structure is then determined with reference to the sensor element structure giving the best comparison with the yarn image. However, a plurality of sensor types for a plurality of parameters also can be used, and the signals of the sensors for the various parameters can be correlated. In such a case, a sensor signalling even very poor correspondence for a specific parameter can, under certain circumstances, make a contribution for determining the structure sought.

Alternatively, according to the invention, the yarn may be illuminated with monochromatic light, and the light reflected by the yarn may be guided through a lens onto a sensor arranged in the focal plane of such lens and having a plurality of sensor elements of differing structural arrangements. The signals of the individual sensor elements are tested for correspondence with the examined structure, and the examined structure is determined by processing the signals supplied by the sensor elements.

Apparatus according to the invention is characterized by a sensor, which is constructed from a plurality of photoelectric cells of differing structuring and by an evaluation device containing a correlation matrix for processing the signals supplied by the sensor elements.

A preferred embodiment of the apparatus according to the invention is characterized in that the sensor elements are formed by photoelectric cells arranged on an integrated photochip, and in that the photochip additionally contains an integrated circuit for evaluation.

BRIEF DESCRIPTION OF THE DRAWINGS

The invention will be explained in more detail below with reference to an exemplary embodiment depicted in the drawings, in which.

DETAILED DESCRIPTION OF PREFERRED EMBODIMENT

Figures 1, 2:
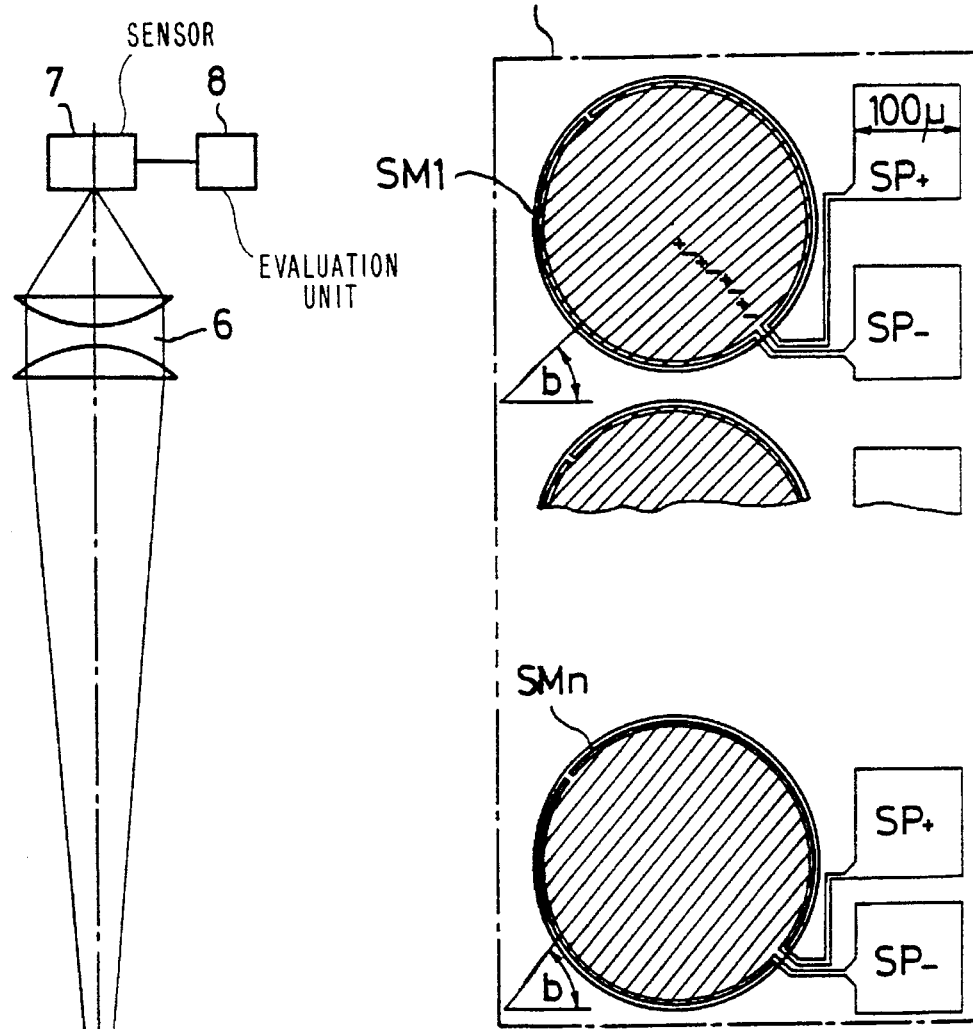
FIG. 1 shows a diagrammatic representation of an apparatus according to the invention.
FIG. 2 shows a greatly enlarged cutout from the surface of the sensor of the apparatus of FIG. 1.

FIG. 1 shows, at the bottom, a piece of a yarn G which is conveyed by transport means (not shown) in the direction of the arrow P through an apparatus for determining the surface structure of the yarn G. The yarn may move continuously with the measurement being carried out on the moving yarn, or the yarn may move in steps with the measurement being carried out when the yarn is stationary. In both instances, the yarn G is guided via a thread guide 1 which serves for positioning the yarn in the beam path of the apparatus and for stabilizing its position.

The individual turns (e.g., twist) of the yarn G have a pitch "a" in relation to the yarn axis. When the yarn G is illuminated perpendicularly to its axis, reflections occur and these are imaged on a suitable sensor in order to determine the surface structure of the yarn. Although the twist of the yarn is a primary feature of yarn surface structure, more complicated structural features, such as, for example, fiber crossovers or wrapper fibers, also have highly typical structures and are also appropriate for evaluation.

The yarn G is illuminated vertically from above by a light source 2 via a condenser 3 and a beam-splitting mirror 4. The light reflected by the yarn surface passes through a beam-splitting mirror 4 and an objective lens 5 to a condenser 6 which collects the light and concentrates it on a photoelectric sensor 7. This gives rise to an imaging of the surface structure of the yarn G on the sensor 7. An evaluation unit 8 connected to the sensor 7 serves to provide a more detailed evaluation of the structure. The yarn G, of course, also can be illuminated directly.

To make it possible to determine the surface structure of the yarn G, the sensor 7 possesses a plurality of photocell arrangements of differing structural arrangements on its surface. These structural arrangements represent images of typical types corresponding to the structure to be determined. The image of the yarn surface is compared simultaneously or sequentially with these individual structure types and, in a kind of correlation method, it is established which of the structure types corresponds best to the structure being evaluated.

Herein, the term "structure in the region of the surface" is used to mean not only the structure of the actual yarn surface but also that of the yarn edge, including fibers projecting from this. The projecting fibers within a specific distance from the yarn edge may be taken into account, including possible inclusions. Also, impurities, especially those which are caused by foreign fibers included in the yarn, may be taken into account. Such impurities can be recognized by their form and/or their color.

In the simplest case, the determination of structure involves the measurement of the fiber angle "a" on the yarn surface. Where yarns produced on ring spinning machines are evaluated, the twist can be computed from the angle "a" and from the yarn diameter. For this instance of use, the sensor 7 is designed preferably according to the representation of FIG. 2, in that a plurality of stripe patterns SM1 to SMn of photocells (in practice, up to 20 or more) differing from one another in the angle "b" to the horizontal are arranged on an integrated photochip.

In FIG. 2, the angle "b" in the striped pattern SM1 amounts to 40°, and in the stripe pattern SMn it amounts to 50°. The width of the individual stripes is on the order of the diameter of the imaged fibers. The photocurrents generated in the individual stripe-shaped photocells are guided alternately to one of two circuit points SP+ and SP– and are summed there. That is to say, the even-numbered photocells are guided to one circuit point and the odd-numbered photocells are guided to the other circuit point SP+ and SP–, respectively. In the evaluation unit 8, which is preferably formed by an IC integrated on the photochip, the difference between the sum currents of the two circuit points is determined and evaluated. This absolute difference averaged over time is a measure of the orientation of the fibers, and it is at its highest in that stripe pattern, the angle "b" of which best corresponds to the fiber angle "a" on the yarn surface. The exact value of the fiber angle "a" is obtained by interpolation from the differences between the sum currents of the individual stripe patterns.

The method described, which corresponds to high-pass filtering (gradient formation) in local space, is independent of movement and functions equally for a stationary and for a moving yarn G. If only a single slit-shaped photocell is used for each angle, instead of a stripe pattern, the measurement is dependent on the movement, in that, with a moved yarn a time-dependent signal is obtained for each photocell. In this case, the light reflected form the yarn is filtered in the time domain by a high-pass filter, preferably one with an adaptive frequency limit, whereby a signal representing the arrangement of fibers in the yarn will be obtained. For this purpose, the approximate yarn speed must be known. These high-pass filtered signal amplitudes of the individual photocells are then interpolated linearly.

Finally, the yarn twist is determined from the fiber angle "a", determined by means of one of the two sensor types described, and from the diameter of the yarn G. The measurement of the diameter takes place preferably by means of a series cell (photocell row, CCD row, photodiode row or transistor row) likewise contained on the photochip. Instead of a simple linear pattern, photocell structures of any sensitivity can be produced by means of an additional absorbing mosaic print. It is possible to compute any fixed local filter theoretically and then produce it in the local space. Thus, for example, a rectangular filter in frequency space becomes a $\sin(x)/x$ filter in local space by Fourier transformation. The determination of the yarn diameter makes it possible to regulate the sensor or the optics in such a way that the latter are always aligned with the yarn center.

In order to record and determine other complicated surface structures of the yarn, the photocell can be provided with images of typical features of such structures by applying such images as photocells to the photochip. Structures of this type can be, for example, photocells in the form of a St. Andrew's cross for fiber crossovers. During measurement, the image of the yarn surface runs over the photocell arrangement. As soon as the yarn contains typical structural features in the manner of the photocell arrangement and these are imaged on the sensor, a clear signal deflection will take place in the respective photoreceivers of the same structure, whereas receivers having unlike structures generate no signal deflection. At the same time, the size of the generated signal corresponds to the product of cross-correlation times light contrast between the two structures. As a result of the simultaneous evaluation of the correlation signals from a plurality of structured receivers of this type, the yarn structures can be classified.

The use of one or more photocell rows affords the additional possibility of examining the yarn edge. This can be helpful for recognizing wrapper fibers. These form a wavy yarn edge and lie flush on the yarn body. Hence, they differ from projecting fibers. In addition, the yarn position can be determined by means of this photocell row, and in the event of abnormally large fluctuations of the yarn diameter and/or of the yarn position, a decision can be made as to whether the examined yarn is within the valid measuring range.

The yarn edge can be seen particularly well by transmitted light. In contrast, the yarn surface can best be seen by incident light. Hence, the use of at least two different types of illumination or illumination devices is desirable. These can carry out the measurements from one and the same point by the shopping mode or from different points. In the latter case, synchronization of the two types of measurement must be carried out.

For imaging an identical yarn piece on different sensors, lens arrangements in row or matrix form, so-called lens arrays, can be used. These also can be designed for holographic images. The evaluation of holograms of the surface structures can be carried out by means of neuronal networks, with which various structural parameters could be examined and evaluated. These various parameters span a multidimensional feature space in which a specific structure forms a limited subspace.

Diffractive optical elements and lens arrays for the imaging of one and the same yarn piece on a plurality of detectors can easily be put into practice when a laser is used as an illumination source. As is known, a laser system works with monochromatic and coherent light. The use of monochromatic light and a lens ensures that the Fourier transformation of the local image lies in the focal plane of the respective lens. As a result of this property, optimum filters for structuring also can be defined in the Fourier plane and can be embodied as a photocell structure. The advantage of this is that the yarn position and depth of definition do not play an important part, because the transform is independent of position.

What is claimed is:

1. Method for determining the structure of yarns in the region of their surface, comprising imaging a surface of a yarn having a surface structure on a sensor that includes a plurality of sensor elements of differing structural arrangement, comparing signals of individual sensor elements for correspondence with the imaged surface structure of the yarn, and processing the signals supplied by the sensor elements to determine the surface structure of the yarn.

2. Method according to claim 1 for determining the structure of yarns in the region of their surface, wherein the surface of the yarn is imaged by illuminating the yarn with monochromatic light which is reflected by the surface of the yarn, and directing the reflected light through a lens onto said sensor, said sensor being arranged in the focal plane of said lens.

3. Method according to claim 1 for determining the structure of yarns in the region of their surface, wherein the surface structure determined is yarn twist, the determination of the yarn twist including determining a fiber angle on the surface of the yarn by way of said sensor elements, determining the diameter of the yarn, and computing the yarn twist on the basis of the determined fiber angle and diameter.

4. Method according to claim 1 for determining the structure of yarns in the region of their surface, wherein surface structures of yarns are determined by providing on said sensor images of features typical of said surface structures.

5. Method according to claim 4, wherein the surface structures of the yarn to be determined include yarn impurities.

6. Apparatus for determining the structure of yarns in the region of their surface, comprising a sensor, a device for imaging a yarn surface onto the sensor, said sensor having a plurality of sensor elements of differing structural arrangement relating to a structure of the yarn surface, and an evaluation device operatively associated with said sensor for processing signals supplied by the sensor elements.

7. Apparatus according to claim 6, wherein the sensor elements are formed by photocells arranged on an integrated photochip, the photochip containing integrated circuits for evaluation.

8. Apparatus according to claim 7, wherein the sensor elements are formed by a striped pattern of photocells which generate photo currents, the striped pattern of photocells identifying different surface structures, the photo currents of individual photocells being guided alternately to one of two circuit points for summing the photo currents, and wherein differences between the sum of photo currents at the two circuit points indicate correspondence of the surface structure of the respective striped pattern with the structure on the imaged yarn surface.

9. Apparatus according to claim 6, wherein the device for imaging the yarn surface includes a light source for illuminating the yarn, and an objective lens and condenser for collecting light reflected from the yarn surface and directing the reflected light to the sensor.

* * * * *